United States Patent
Norton et al.

(10) Patent No.: US 8,123,750 B2
(45) Date of Patent: Feb. 28, 2012

(54) APPARATUS AND METHODS FOR REMOVAL OF INTERVERTEBRAL DISC TISSUES

(75) Inventors: Britt K. Norton, Eden Prairie, MN (US); Christine M. Horton, Prior Lake, MN (US); Jeremy J. Ling, St. Paul, MN (US)

(73) Assignee: Corespine Technologies, LLC, Minneapolis, MN (US)

( * ) Notice: Subject to any disclaimer, the term of this patent is extended or adjusted under 35 U.S.C. 154(b) by 374 days.

(21) Appl. No.: 12/570,824

(22) Filed: Sep. 30, 2009

(65) Prior Publication Data

US 2010/0100098 A1    Apr. 22, 2010

Related U.S. Application Data

(63) Continuation-in-part of application No. 11/207,094, filed on Aug. 17, 2005, now abandoned.

(51) Int. Cl.
*A61B 17/00* (2006.01)
(52) U.S. Cl. .................. 606/80; 606/114; 606/79
(58) Field of Classification Search ............. 606/79–81, 606/86 R, 114–115, 82–85, 167, 180, 170, 606/279; 408/127
See application file for complete search history.

(56) References Cited

U.S. PATENT DOCUMENTS

| | | | |
|---|---|---|---|
| 4,646,738 A * | 3/1987 | Trott | 606/170 |
| 5,217,479 A * | 6/1993 | Shuler | 606/180 |
| 5,320,635 A * | 6/1994 | Smith | 606/180 |
| 5,383,884 A * | 1/1995 | Summers | 606/170 |
| 6,533,749 B1* | 3/2003 | Mitusina et al. | 604/22 |
| 7,244,263 B2* | 7/2007 | Robison et al. | 606/170 |
| 7,276,074 B2* | 10/2007 | Adams et al. | 606/170 |
| 7,338,495 B2* | 3/2008 | Adams | 606/79 |
| 7,922,720 B2* | 4/2011 | May et al. | 606/80 |
| 7,927,361 B2* | 4/2011 | Oliver et al. | 606/279 |
| 2005/0159767 A1* | 7/2005 | Adams et al. | 606/180 |
| 2007/0149975 A1* | 6/2007 | Oliver et al. | 606/79 |

* cited by examiner

*Primary Examiner* — Eduardo C Robert
*Assistant Examiner* — Jan Christopher Merene
(74) *Attorney, Agent, or Firm* — Vidas, Arrett & Steinkraus P.A.

(57) ABSTRACT

Apparatus and methods for removing tissue from an intervertebral disc are disclosed. The apparatus can include an elongated guide tube, a rotary cutting member and a drive shaft. Other apparatus can include an elongated guide tube, an inner guide tube, a cutting head, a rotary cutting member and a drive shaft. The elongated guide tube has a bendable end. The apparatus are generally configured to extend and withdraw a rotary cutting member while controllably bending the bendable end of the guide tube.

16 Claims, 6 Drawing Sheets

Section 8-8

APPARATUS AND METHODS FOR REMOVAL OF INTERVERTEBRAL DISC TISSUES

CROSS REFERENCE TO RELATED APPLICATIONS

The present application is a continuation-in-part of U.S. patent application Ser. No. 11/207,094 filed Aug. 17, 2005 now abandoned. All of the preceding patents and patent applications are incorporated herein by reference in their entirety.

BACKGROUND OF THE INVENTION

1. Field of the Invention

The present invention relates to removal of intervertebral discs and, more particularly, to apparatus and methods for removal of the nucleus pulposus of an intervertebral disc.

2. Description of the Related Art

The spine is made up of twenty-four bony vertebrae, each separated by a disc that both connects the vertebrae and provides cushioning between them. The lumbar portion of the spine has five vertebrae, the last of which connects to the sacrum. The disc is comprised of the annulus, which is a tough, layered ligamentous ring of tissue that connects the vertebrae together, and the nucleus, a gelatinous material that absorbs water and is fed through the endplates of the vertebrae. In a healthy disc, the nucleus is pressurized within the annulus much like the air is pressurized within an automobile tire.

Degenerative disc disease (DDD) is a condition that affects both structures of the disc, and is usually thought of as a cascade of events. In general, DDD is characterized by a weakening of the annulus and permanent changes in the nucleus, and may be caused by extreme stresses on the spine, poor tone of the surrounding muscles, poor nutrition, smoking, or other factors. In DDD, the nutrient flow to the nucleus is disrupted and the nucleus loses water content. As the nucleus dehydrates it loses pressure, resulting in a loss of disc height and a loss in the stability of that segment of the spine. In the lumbar spine, as the degenerative cascade continues, the annulus may bulge and press on a nerve root, causing sciatica (leg pain) among other problems. The loss of disc height can also result in leg pain by reducing the size of the opening for the nerve root through the bony structures of the spine. As the disc loses height, the layers of the annulus can begin to separate, irritating the nerves in the annulus and resulting in back pain.

Surgical treatment for early DDD, where the pain is primarily leg pain, is usually a discectomy where some the nucleus material is removed to reduce the bulging of the disc and the pressure on the nerve root. For more severe cases of DDD, where the disc has completely collapsed and/or where a discectomy did not have long-term success, the surgical treatment standard of care is fusion of the vertebrae through the use of plates, rods, pedicle screws, and interbody fusion devices. The trend in fusion surgery is an increasing use of less invasive techniques, which reduce post-operative pain and patient recovery times by reducing the amount of tissue disruption during the surgery. Recently, surgeons and industry have been looking for ways to interrupt the degenerative cascade earlier in the disease process, and for methods that retain motion at the affected disc in patients with more advanced disease. The field of spinal arthroplasty represents a significant emerging market in spinal surgery, and includes devices known as total disc replacements (TDR) and partial disc replacements (PDR) where only the nucleus of the disc is replaced by a prosthetic device.

Surgical treatment for early stage disease that involves primarily leg pain as a result of a herniated disc is currently limited to a simple discectomy, where a small portion of the disc nucleus is removed to reduce pressure on the nerve root, the cause of the leg pain. While this procedure is usually immediately successful, it offers no means to prevent further degeneration, and a subsequent herniation requiring surgery will occur in about 15% of these patients.

The method currently used for most intervertebral fusion procedures involves placing an interbody fusion device in the disc nucleus cavity, which supports and stabilizes the anterior column of the spine. Small pieces of the patient's own bone, taken either from the bone removed from the spine during surgical access or from a donor site such as the iliac crest, are packed in and around the fusion device to speed the subsequent bone growth process. It has been well-established that any nucleus material remaining in the disc space following the fusion surgery will likely interfere with the fusion process by acting both as a mechanical and biological barrier to bone growth.

Current designs for nucleus replacement devices are typically not attached to the nucleus or vertebra, and are free to move within the nucleus cavity. Much like the healthy nucleus, these devices are subjected to the high forces and the twisting and bending motions that must be endured by the spinal structures, and some device movement is expected. Current PDR devices have a known complication of excessive device movement, however, and can move back out the annulus at the site of implantation. This device extrusion can occur in over 25% of cases for some designs. While the effect of the complication is not life threatening, the response is another surgery to reposition or replace the PDR, or to remove it altogether and likely replace it with a total disc replacement or a fusion procedure. There is mounting evidence that the nucleus material left in the disc cavity, even after an exhaustive removal procedure, can push against even a well-positioned PDR and be the cause of many of the device extrusions. When a posterior approach is used for removal, the remaining nucleus material left behind can push against a PDR. While more of this material could be removed if the disc is accessed via a lateral or an anterior approach, current information indicates that most spine surgeons prefer to use the posterior approach.

The trend in TDR designs, like the trend in fusion procedures, is to minimize tissue trauma by reducing the invasiveness of the procedure. These devices typically rely on bony in-growth of the vertebrae-contacting portions of the device with the vertebral endplates to assure the devices remain in proper position following implantation. As with fusion procedures, any remaining nucleus will likely have a negative impact on the process of bony in-growth of the device and may lead to an increased incidence of device movement.

For intervertebral fusion, TDR and PDR, among other procedures, implantation site preparation typically involves removal of the nucleus. A wide range of devices have been developed for this removal procedure. However, surgeons have historically utilized an array of pituitary rongeurs and curettes for the various procedures requiring removal of the nucleus pulposus or portions of the nucleus pulposus. A rongeur is a single-hand "pistol-grip" actuated mechanical instrument with two cup-shaped hinged jaws that cut and rip tissue. The rongeur is provided in a variety of configurations including "up-biting"; straight; and "down-biting", and can be found in a variety of lengths, widths, and with razor or serrated jaws. A curette is a rigid tool with a sharpened scraping tip that is often in the shape of a cup or ring, and also is provided in a variety of configurations. Using the preferred posterior access to the intervertebral disc with a rongeur or curette limits the useful range of motion within the disc. The bony structure of the posterior spinal elements, even though partially removed to provide access for implantation of the interbody device such as a fusion implant or PDR, typically limits the angles through which the rongeur or curette can be maneuvered. This limitation of movement serves to limit the amount of nucleus material that can be removed. More importantly, the limitation on movement may not allow adequate removal of material contralateral to the annular access, preventing optimal position for a PDR and inhibiting bone growth for a fusion procedure. Further, the use of a rongeur or curette requires constant insertion and removal to clean the nucleus material from the tip of the device, resulting in dozens of insertion/removal steps to remove an adequate amount of material from the nucleus. This can increase the trauma to the surrounding annulus tissue and increase the risk of damaging the endplates.

An additional significant limitation of both the rongeur and curette is the ability to easily remove the important annular tissue. Surgeons typically do not try to remove the entire nucleus in simple discectomy procedures, or intentionally remove annulus in preparation for fusion procedures; the annulus is intended to be preserved to help stabilize the spine as part of the treatment. Furthermore, most surgeons perform these procedures using tactile feedback to judge their position in the disc space and the type of material they are removing. These surgeons are "working blind" and rely on their experience and training to determine when to keep removing tissue or when to stop. In this respect, a surgeon's "feel" for the tissue, or ability to distinguish softer nucleus tissue from tougher annulus tissue, may not be well developed and PDR site preparation may result in significant trauma to the annulus. Important tissues surround the annulus, such as nerve roots that descend from the spinal column, the lumbar nerve plexus and major blood vessels including the aorta. Damaging these tissues can result in paralysis and death, and the risk of these complications is recognized as inherent in spine surgery.

In contrast to spinal fusion procedures, where the cartilage layer on the endplates of the vertebrae that contact the nucleus is removed along with the nucleus (to allow blood from the cancellous portion of the vertebrae to enter the disc space and provide the nutrients and proteins necessary for bone growth), nucleus replacement procedures seek to maintain the integrity of the cartilage layer to prevent the bone growth process from occurring. Rongeurs and curettes used to remove the nucleus have the capability to easily remove the cartilage, resulting in a potential for unwanted damage of the cartilage and subsequent growth of bone throughout the disc and vertebral fusion in a procedure where the intent is to maintain disc motion.

A range of more sophisticated devices for removing nucleus has been developed, however, the adoption of these devices has been very limited. Some of the more intricate devices utilize mechanized cutting mechanisms for removal of material from the nucleus pulposus. Frequently, these devices require suction and/or irrigation to remove material during the procedure.

One device uses a guillotine-style assembly that cuts nucleus material, aspirates the material into the instrument tip, and then evacuates the cut material is through the instrument. Movement of the guillotine assembly is automated and controlled by a mechanism in the handpiece of the instrument. The continuous removal of tissue without the need to repeatedly insert and remove the instrument minimizes trauma to the surrounding tissue. The guillotine type assembly is found on a straight, stiff device, that is intended for a minimally invasive, percutaneous approach. Because of their stiffness, although the devices may be somewhat effective for a lateral or anterior surgical approach for PDR implantation, they are generally not usable for nucleus removal utilizing a posterior approach and their small size prevents efficient removal of nucleus material from the entire disc cavity.

Other devices have utilized an Archimedes type screw to pull nucleus material into the catheter and shear it when it reaches the tip of the catheter. Continued collection of nucleus material by the rotating Archimedes type screw pushes the sheared material through the catheter and into a collection chamber. While less complicated to use than the previously discussed guillotine type assembly, the devices utilizing the Archimedes type screw typically have the similar maneuverability and bulk tissue removal disadvantages. Further, these devices can relatively easily be directed into and through the annulus of the intervertebral disc being treated.

Still other systems have used a high-pressure stream of water to remove nucleus material. In one device, the high-pressure stream of water produces a vacuum which pulls nucleus material into the stream. The high-pressure stream of water then cuts the nucleus material and pulls the material through a catheter to a collection bottle. Among other disadvantages, such systems are expensive. Further, the tip of the instrument can be bent only slightly since its design relies heavily on the use of a stiff metal tube to withstand the high pressure of the water stream, such that its lateral reach when used via the posterior approach is still very limited. Further, since the water stream is very narrow, successful nucleus removal can be technique dependent and time consuming.

Still other devices utilize radio frequency (RF) energy or plasma directed through electrodes for tissue resection and vessel cauterization in preparation for implanting a PDR. These devices typically include an RF generator that can be used with a variety of different types and shapes of electrodes. These devices are typically stiff and have little lateral reach when used making them relatively ineffective for use through the posterior approach. Further, the RF ablation technology can resect annulus or endplate cartilage as easily as nucleus material, as well as other critical nerve and vascular tissues surrounding the annulus.

Still other devices utilize lasers to remove material from the nucleus pulposus. These lasers are typically transmitted through a laser fiber positioned within a multi-lumen catheter. These multi-lumen catheters have also included additional components such as imaging fibers, illumination fibers, and irrigation ports. Further, the tip of these catheters can be slightly steerable. Although steerable, the bend radius of the catheters typically prevents them from being useful for removing nucleus near the annulus access and limits their reach into the area of the disc contralateral to the annular access. Further, the effective radius of laser beam from these devices is typically only 0.5 mm, making removal of large amounts of nucleus very difficult and time consuming. Detrimentally, lasers can resect annulus or endplate cartilage as easily as nucleus material. Since the tip of the catheter is typically not protected, the laser beam has the ability to easily penetrate and damage the annulus and endplate tissue, as well as other critical nerve and vascular tissues surrounding the annulus.

Other devices for nucleus removal are also available. However, these technologies possess their own limitations for the unique needs of annulus repair and PDR device site preparation. The limitations of these devices, along with those of the pituitary rongeur, are driving the need for a more advanced instrument for nucleus removal.

In the case of the spinal disc the three materials proximate to each other, the nucleus, annulus and cartilage, each have different biological constituents and mechanical properties. The nucleus is primarily made up of proteoglycans such as hyaluronic acid, a material that swells and is extremely slippery upon contact with water. In a degenerated disc being treated with a surgical procedure, the nucleus typically has experienced significant water loss even though the hyaluronic acid is still present and still able to absorb water. In hydrated form, the nucleus is extremely slippery and has been characterized as gelatinous; in dehydrated form it has adhesive qualities (is "sticky") and has been likened in texture to "crab meat". In either case, nucleus tissue is a relatively soft, mobile material. The annulus is a tough ligamentous structure comprised primarily of long collagen chains. Extreme degeneration can affect the toughness of the annulus, but it is always less elastic and far less mobile than the nucleus tissue. The nature of the annulus can be characterized as a reinforced rubber. While also containing collagen, the cartilage tissue is different from the nucleus and annulus and exhibits properties similar to a harder, polyethylene-like plastic material. The cartilage is the least mobile tissue of the three found in the disc space. The disparate properties of these materials, especially of the mobility of the nucleus tissue compared to the relative immobility of the annulus and cartilage, allows for an appropriately designed cutting instrument to take advantage of these differences for removal of the nucleus while leaving the annulus and cartilage undamaged.

Thus, current cutting instruments have many shortcomings including the shortcomings discussed above.

SUMMARY OF THE INVENTION

Apparatus and methods in accordance with the present invention may resolve many of the needs and shortcomings discussed above and will provide additional improvements and advantages as will be recognized by those skilled in the art upon review of the present disclosure. Most surgeons are used to "working blind" in the disc space. A cutting instrument is disclosed that not only has the ability to discriminate between tissues desired for removal and those intended to be left intact, but also has the ability to remove these tissues in an automatic fashion instead of through repeated insertion and removal of the instrument, as is the case with rongeurs and curettes. The cutting instrument that can safely cut only the more mobile tissue allows the instrument to be used in a manner where the cutting tip is actively put into contact with the less mobile tissue in order to assure as much of the more mobile tissue is removed. With most cutting devices, this type of intimate contact is discouraged in order to prevent damage to the less mobile tissues.

In one exemplary embodiment, the present invention may provide an apparatus for removing tissue from an intervertebral disc including an elongated guide tube, an inner drive tube, a cutting head, a rotary cutting member and a drive shaft, and an irrigation port located on the exterior of the cutting head. The elongated guide tube defines a lumen. The lumen extends through the elongated guide tube from a proximal opening at a proximal end of the elongated guide tube to a distal opening at a distal end of the elongated guide tube. The distal portion of the elongated guide tube and lumen is configured to reversibly bend when actuated by the user. The lumen may also extend linearly over a linear section extending between the bend and the distal opening of the elongated guide tube. The bend can direct the lumen and the distal opening laterally from the longitudinal axis of the elongated guide tube. The cutting tip includes the cutting head and the rotary cutting member. The cutting tip is slidably received within the distal opening at the distal end of the elongated guide tube. The cutting head is configured to contain the rotary cutting member while allowing it to rotate about the axis of the elongated guide tube. The cutting head may include a shape configured to be able to pass through the tissue of the nucleus pulposus but to be only atraumatic to the tissue of the annulus fibrosus. The cutting head defines an anterior cavity at a distal end of the cutting head. The cutting head further includes at least one tissue receiving opening on its distal end, the tissue receiving opening extending from an outer surface of the cutting head to the anterior cavity. The tissue receiving opening receives materials of an intervertebral disc as the cutting head is advanced through the intervertebral disc. The rotary cutting member is positioned within the anterior cavity of the cutting head. The rotary cutting member is configured to cut and/or abrade material received through the tissue receiving opening. The inner drive tube is slidably received within the lumen of the elongated guide tube. The inner drive tube is secured to the rotary cutting member to confer rotational movement to the rotary cutting member while positioned within the anterior chamber of the cutting head. The irrigation port defines a tube with a distal and a proximal opening. The irrigation port may be connected at the proximal opening to an irrigation tube that extends along the exterior of the elongated guide tube to the proximal end of the elongated guide tube. The proximal portion of the irrigation tube may be configured to be connected to an irrigation fluid source. The proximal end of the inner guide tube may be configured to be connected to a vacuum source.

The foregoing discussion discloses and describes a merely exemplary embodiment of the present invention. Upon review of the specification, one skilled in the art will readily recognize from such discussion, and from the accompanying drawings and claims, that various changes, modifications and variations can be made therein without departing from the spirit and scope of the invention as defined in the following claims.

Figure 1:
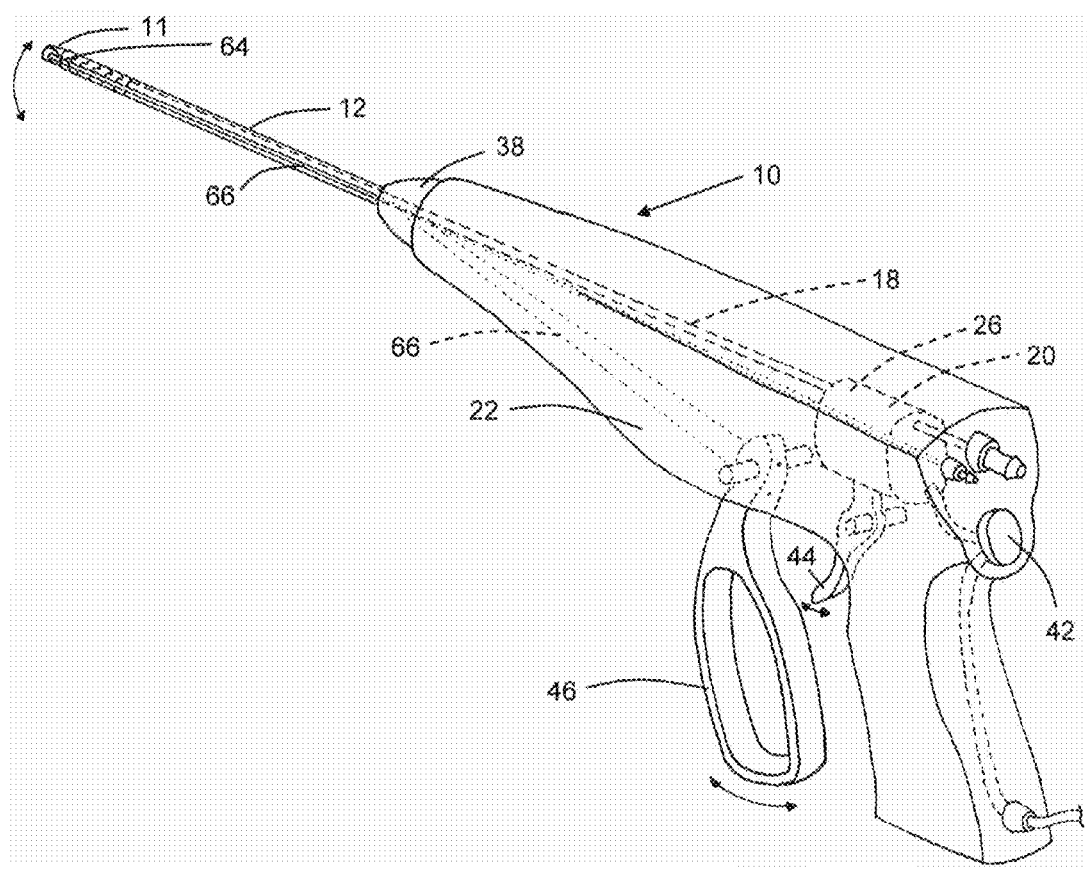
FIG. 1 illustrates a perspective view of an embodiment of an apparatus, in accordance with an example embodiment.

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings as it would appear to a person viewing the drawings and utilized only to facilitate describing the illustrated embodiment.

DETAILED DESCRIPTION OF THE INVENTION

Figure 2:
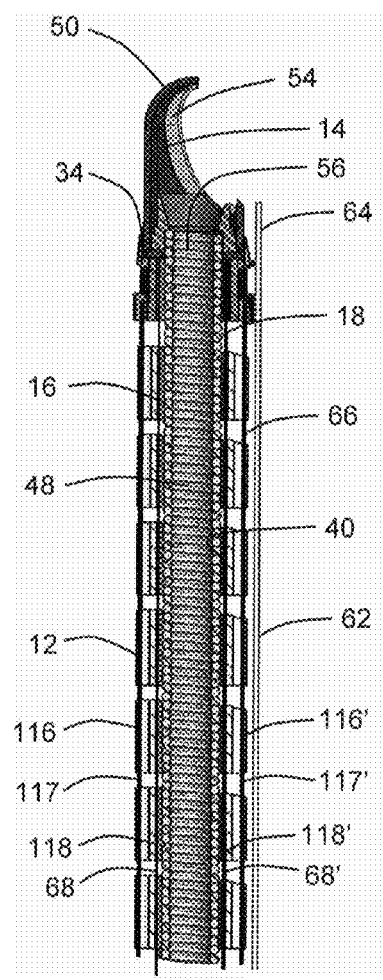
FIG. 2 illustrates a cross-section of an embodiment of the distal portion of an apparatus, in accordance with an example embodiment.
Figure 3:
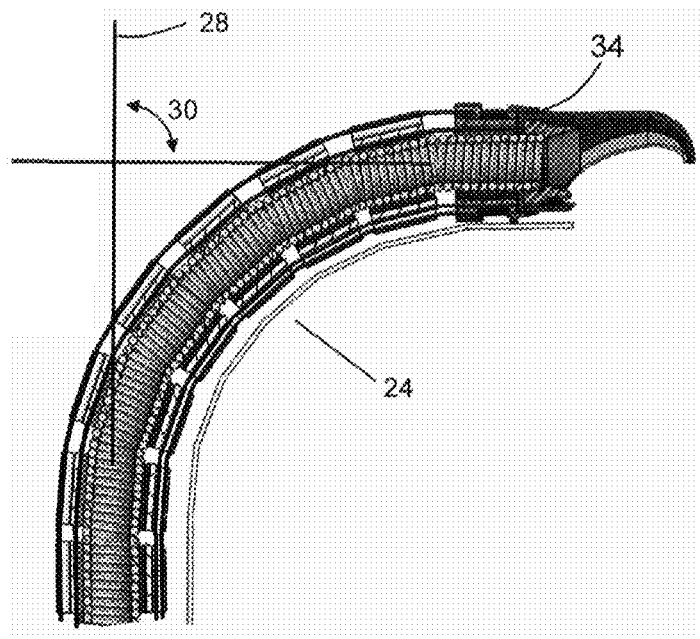
FIG. 3 illustrates a cross-section of an embodiment of the distal portion of an apparatus in one possible cutting orientation, accordance with an example embodiment.

Referring to FIGS. 1, 2 and 3, the present invention provides an apparatus 10 and methods for removal of materials from an intervertebral disc positioned between adjacent vertebral bodies within the spine of a patient. The apparatus 10 generally provides cutting tip 11 at the distal tip of an elongated guide tube 12 for accessing and removing tissues from an intervertebral disc. The apparatus 10 is generally configured to access the intervertebral disc in a minimally invasive manner. Generally, cutting tip 11 is configured to extend from and retract into the elongated guide tube 12 while rotary cutting member 14 is rotating to remove or facilitate the removal of nucleus pulposus tissue from the intervertebral disc. The apparatus 10 is typically generally configured to permit posterior access to the intervertebral disc wherein elongated guide tube 12 may additionally possess sufficient flexibility to permit the bending of the elongated guide tube 12 around the anatomical structures of the spine.

Apparatus 10 in accordance with the present invention generally includes an elongated guide tube 12 having a cutting tip 11 as illustrated generally throughout the Figures for exemplary purposes. As illustrated in FIGS. 2 and 3, the rotary cutting member 14 may be positioned within an anterior chamber 54 of a cutting head 50. The cutting member 14 and the cutting head 50 may be extended from or retracted into a lumen 16 defined by the elongated guide tube 12. Typically, the rotary cutting member 14 and the cutting head 50 will be extended and retracted together with the rotary cutting member 14 being retained within an anterior chamber 54 of the cutting head 50 during operation.

An inner drive tube 18 is also provided within the lumen 16 of elongated guide tube 12. A distal end of the drive shaft 18 is operably connected to the rotary cutting member 14 to confer a rotational force upon the rotary cutting member 14. The drive tube 18 may extend through a posterior passage 56 of the cutting head 50 to connect to the rotary cutting member 14 contained within the anterior chamber 54 of cutting head 50. In one aspect, the drive tube 18 may rotate the rotary cutting member 14 relative to the anterior chamber 54. The drive tube 18 is typically operably connected to a motor 20 at a proximal end of the drive shaft 18. However, the drive tube 18 may be otherwise operably connected to the motor 20 to confer a rotational motion upon the drive tube as will be recognized by those skilled in the art upon review of the present disclosure. Motor 20 may be an electrical motor, a pneumatic drive system, a hydraulic drive system, or other system or motor as will be recognized by those skilled in the art upon review of the present disclosure. To facilitate the extending and retracting of the rotary cutting member 14, the motor 20 may be movable relative to the elongated guide tube 12. In one aspect, the motor 20 may be slidably mounted in a housing or handle 22 to which the proximal end of elongated guide tube 12 is secured as illustrated in FIG. 1 for exemplary purposes.

Figure 4:
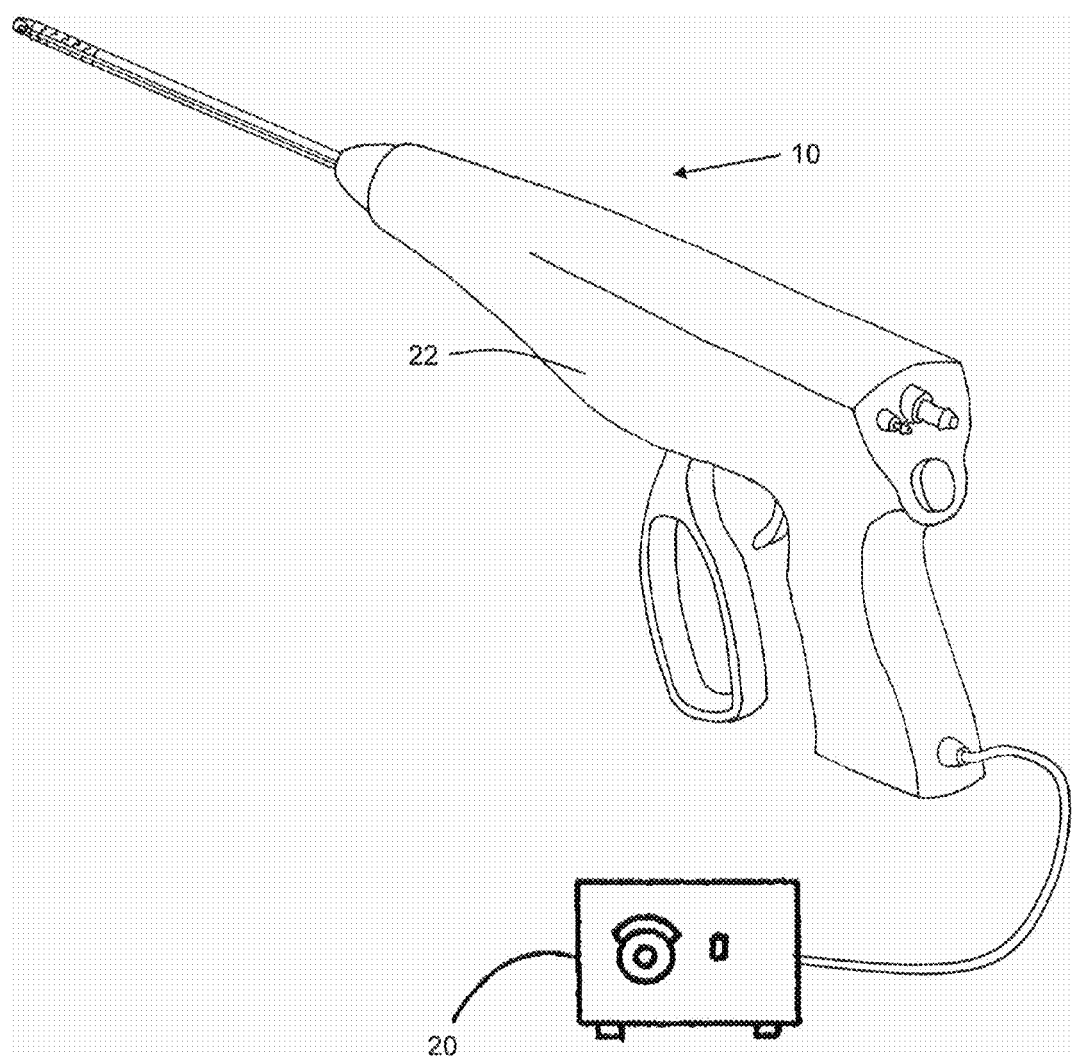
FIG. 4 illustrates a perspective view of another embodiment of an apparatus having a remote rotational drive mechanism, in accordance with an example embodiment.

Housing 22 may be configured to permit a surgeon to grip the housing 22 as a handle to manipulate the distal end of elongated guide tube 12 and/or cutting member 14 to and within an intervertebral disc of a patient. The cutting member 14 may also be movably secured to the distal end of the drive tube 18 to permit extending and retracting of the rotary cutting member 14, the motor 20 may be movably connected to the proximal end of the drive tube 18 to permit extending and retracting of the rotary cutting member 14, or the rotary cutting member 14, drive tube 18 and motor 20 may be otherwise configured to permit extending and retracting of the rotary cutting member 14. In another aspect, the motor 20 may be provided remotely from the apparatus 10 and transfer the rotational motion to drive tube 18 through, for example, a transmission and/or clutch assembly 26 located within housing 22 as illustrated in FIG. 4. Regardless of configuration, a force is conferred upon the rotary cutting member 14 by a drive tube 18 having sufficient torque to permit rotary cutting member 14 to cut through the material of the intervertebral disc at a rate sufficient to remove tissue within the time constraints for a particular procedure or a rate preferred by an operating physician.

Elongated guide tube 12 may be configured from a material which permits a surgeon to properly position the distal portion of the elongated guide tube 12 within an intervertebral disc to remove the desired portions of the intervertebral disc. In one aspect, applications may required that the elongated guide catheter 12 have sufficient flexibility to bend and otherwise flex as the distal end of the elongated guide tube 12 is inserted through a patient into the intervertebral disc. In other aspects, applications may require that the elongated guide tube 12 have sufficient stiffness to permit a surgeon to advance the distal end into the intervertebral disc and to precisely maneuver the distal portion of the elongated guide tube 12 within the intervertebral disc. In still other aspects, applications may require that the elongated guide tube 12 have a variable stiffness along its length. Typically, the material used is polymeric such as a high density polyethylene, PTFE, PEBAX, PEEK or other flexible polymeric material which will be recognized by those skilled in the art. However, the material may be a metal, composite materials or other material selected and configured for access to the intervertebral disc. Alternatively, the elongated guide tube 12 may be configured from a stiff material such as a metal to allow precise positioning and movement of the rotary cutting member 14. The elongated guide tube 12 defines a central lumen 16 that extends along the longitudinal axis 28 of the elongated guide tube 12. In one aspect, the central lumen 16 may include a lubricious coating 40 to reduce friction between the walls of lumen 16 and the drive tube 18. The distal end of the elongated guide tube 12 is configured to provide a reversible bend 24 when actuated by the user which directs the elongated guide tube 12 and the associated lumen 16 laterally at a desired angle 30 from the longitudinal axis 28. The angle 30 is typically between about 60 degrees and 120 degrees from the longitudinal axis 28. In one aspect, the angle 30 of the bend 24 may be about 90 degrees from the longitudinal axis 28 as is generally illustrated in the figures for exemplary purposes. The elongated guide tube 12 has two smaller lumens 116, 116' therein. More specifically, the lumens 116, 116' are within the wall of elongated guide tube 12. The elongated guide tube 12 also includes two control wires or cables 117, 117' positioned within the two smaller lumens 116, 116'. The control wires or cables 117, 117' within the smaller lumens 116, 116' provide a reversible bend feature is for elongated guide tube 12 The wire or cable 117, 117' can be slidably moved within the smaller lumens 116, 116', with the effect of producing the bend 24, at least partially, when one wire is pulled and the other allowed to extend along the length of elongated guide tube 12. Bend lever 46 (see FIG. 1) is configured to perform both of these actions simultaneously when actuated. In this aspect, the degree of bending can be controlled by a user and may be varied during the use of the apparatus 10. The bend is reversible, and elongated guide tube 12 can be straightened, by pulling on the wire that had been allowed to extend while creating bend 24, and allowing the wire that was pulled to create bend 24 to extend, by reversing the motion of bend lever 46. The lumen 16 and bend 24 are configured to generally direct the cutting action of rotary cutting member 14 laterally from the longitudinal axis 28. In one aspect, the distal end of elongated guide tube 12 is configured to include linear section 36 of lumen 16 extending laterally from the longitudinal axis 28 between the end of bend 24 and the distal opening 34 to permit the surgeon to orient and linearly extend the cutting tip 11 through the material of the intervertebral disc in a desired direction. One method of providing an extendibility feature is for elongated guide tube 12 to possess two smaller lumens 118 and 118' therein. More specifically, the lumens 118, 118' are within the wall of elongated guide tube 12. Extension members 68 and 68', which may be wires, rods, or similarly flexible members, are positioned within lumens 118 and 118' and are secured to the proximal portion of cutting tip 11 which can extend relative to lumen 16. Extension members 68 and 68' can be slidably moved within lumens 118 and 118', with the effect of extending cutting tip 11 when pushed distally from housing 22 by actuating extension lever 44. In this aspect, the degree of extension can be controlled by a user and may be varied during the use of the apparatus 10. The extension is reversible, and cutting tip 11 can be pulled back within lumen 16 by reversing the motion of extension lever 44. Alternatively, the extendibility feature can be provided by moving the motor 20 (or combined motor 20/clutch assembly 26) along axis 28 by use of extension lever 44 as illustrated in FIG. 1. In applications for extracting materials from an intervertebral disc, the linear section 36 is typically between 0.5 millimeters and 20 millimeters in length.

Figure 5A:
FIGS. 5A-5D illustrate a formation of a bend in the distal end of the cutting instrument, in accordance with an example embodiment.
Figure 5B:
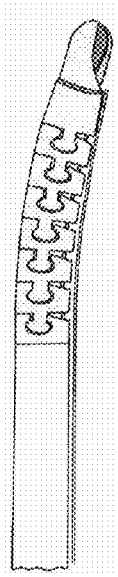
Figure 5C:
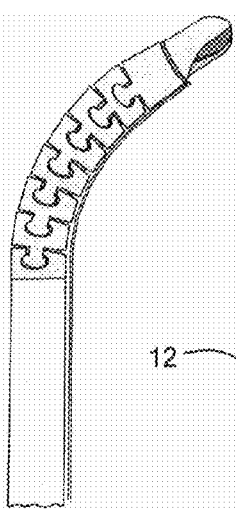
Figure 5D:
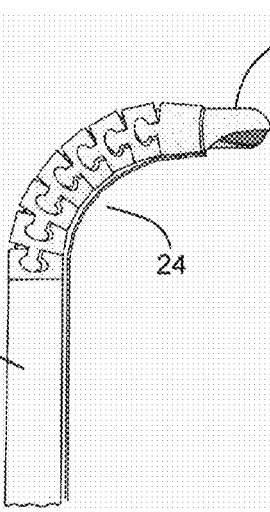
Figure 5E:
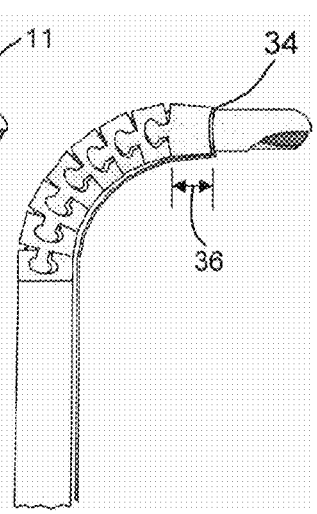
FIG. 5E illustrates the distal end of the cutting instrument having a cutting tip extended from the distal end opening, in accordance with an example embodiment.

The formation of bend 24 is illustrated generally in FIGS. 5a through 5d. The extension of cutting tip 11 from distal opening 34 is illustrated in FIG. 5e.

Figure 6A:
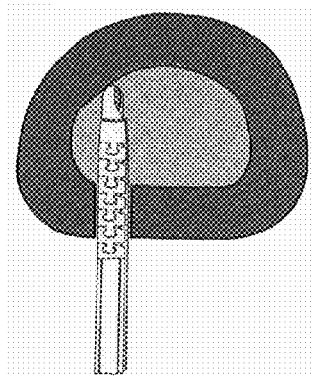
FIGS. 6A-6F illustrate a sequential series of top views of the distal end of a cutting device advancing through the nucleus pulposus of an intervertebral disc, in accordance with an example embodiment.
Figure 6B:
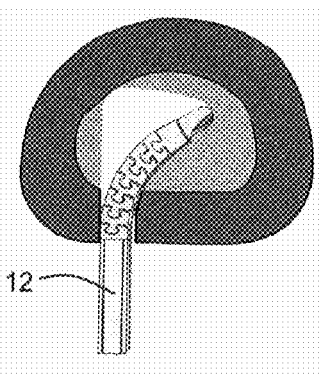
Figure 6C:
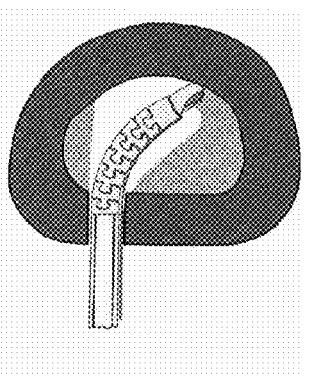
Figure 6D:
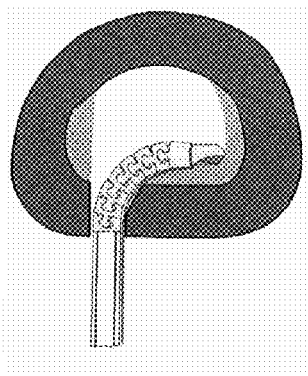
Figure 6E:
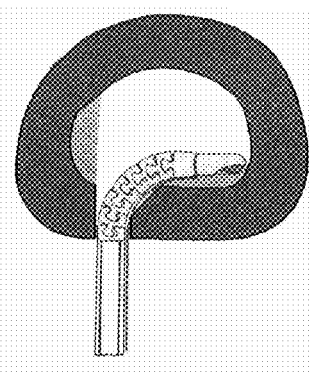
Figure 6F:
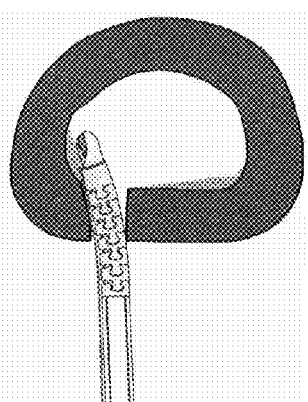

One embodiment of the present invention is illustrated in an exemplary sequence in FIGS. 6a through 6f. The rotary cutting member 14 is shown partially rotated within cutting head 50 in these figures. Housing 22 is not shown, for clarity. Prior to use, the apparatus is connected to a vacuum source (e.g., a vacuum line in the operating room) and the irrigation tube 62 is connected to a source of saline, such as a bag of saline. The saline flows through the irrigation tube 62 and irrigation port 64. The distal portion of apparatus 10 is inserted into the intervertebral disc space through an access in the posterior of the annulus of the disc (see FIG. 6a). The motor is engaged, and the apparatus is in an operable condition. By creating a bend 24 by actuating bend lever 46, cutting tip 11 is pushed into nucleus tissue and nucleus tissue is cut as it is forced into the cutting path of rotary cutting member 14 and as it is pulled into the cutting path of rotary cutting member 14 by the applied vacuum (see FIG. 6b). This sweeping motion is repeated as illustrated in FIGS. 6c and 6d. Tissue proximal to the apparatus axis 28 is removed by periodically partially withdrawing and fully reinserting the apparatus. Tissue adjacent to the vertebral endplates is engaged by the cutting tip by rotating the apparatus about axis 28 while performing the cutting action as in FIGS. 6a through 6d to move the cutting tip out of the plane of the disc. Tissue contralateral to the annulus access is engaged by extending cutting tip 11 as illustrated in FIG. 6e. The apparatus can be rotated about axis 28 in order to engage nucleus tissue adjacent to the annulus access as illustrated in FIG. 6f.

Rotary cutting member 14 is generally configured to cut or otherwise disrupt material to permit the concurrent or subsequent removal of tissue. A wide variety of blade designs may be used to facilitate the cutting of material by the rotary cutting member 14. Upon review of the present disclosure, those skilled in the art will recognize additional cutting configurations for rotary cutting member 14 that may be used in devices in accordance with the present disclosure. The rotary cutting members 14 are typically configured to impart a cutting action on nucleus tissue when the rotary cutting member 14 is rotated about a central axis. The rotary cutting members 14 in accordance with the present invention are generally configured to be advanced through the tissue of the intervertebral disc from the distal opening 34 of elongated guide tube 12. Typically, the rotary cutting member 14 cuts tissue as it extends from the distal opening of the guide catheter. Accordingly, the material of the blades is generally selected to withstand the forces conferred by rotational engagement of tissues of the intervertebral disc. Further, the material of the blades may be generally selected to withstand the forces conferred by the surgeon extending and retracting the blade from the lumen of the elongated guide tube 12. In addition, the material for the blades is selected which will not lose its cutting efficiency by, for example, premature dulling in the course of a typical operation. The drive tube 18 operably couples a motive component conferring rotational movement, such as a motor 20 for example, to the rotary cutting member 14. Drive tubes 18 are frequently in the form of wound coils, tubes, and tubes configured with cuts to provide lateral flexibility but also provide efficient torque transmission. In one aspect, the drive tube 18 may define a drive tube lumen 48. A distal end of the drive tube 18 typically engages the rotary cutting member 14. A drive tube 18 may, typically at a proximal end, be operably engaged with the motor 20, a transmission and/or clutch assembly 26 connected to a motor 20, or to another rotationally motivating component to confer a rotational force to a rotary cutting member. A drive tube 18 in accordance with the present invention is typically of a diameter and configuration to be rotatably received within lumen 16 of elongated guide tube 12. Typically, the drive tube 18 will extend for a length greater than the length of the lumen 16. Such a length can permit the rotary cutting member 14 to be extended beyond the distal opening 34 of lumen 16 to engage a tissue within the intervertebral disc. The drive tubes 18 are typically metals however a range of polymers and other materials may be used as will be recognized by those skilled in the art upon review of the present disclosure.

Figure 7:
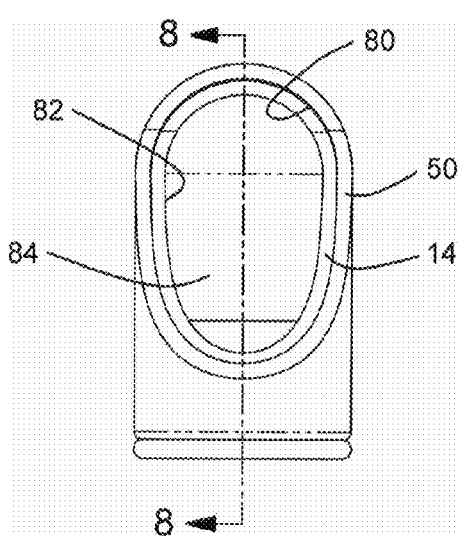
FIG. 7 illustrates a side view of a cutter tip showing a cutter within a cutter head, in accordance with an example embodiment.
Figure 8:
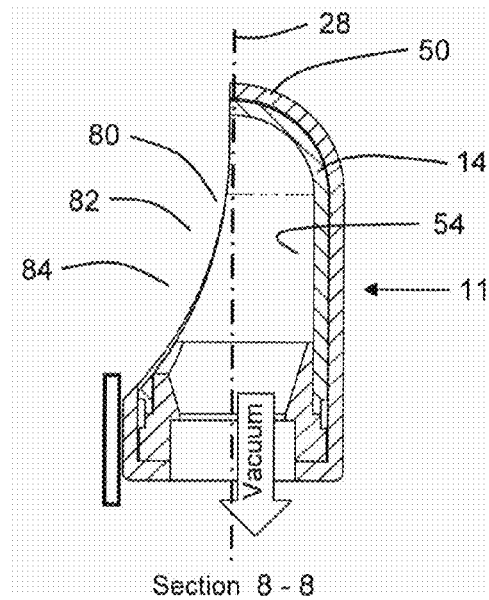
FIG. 8 illustrates a cross sectional side view along line 8-8 in FIG. 7 in accordance with an example embodiment.

The present invention is configured to provide a specific combination of cutting mechanism, cutting edge geometry, cutting speed, negative pressurization, and tissue hydration to provide the ability for continuous removal of nucleus tissue without harming the annulus or cartilaginous endplates. The design of cutter tip 11 is illustrated in FIGS. 7 and 8. Rotary cutting member 14 is rotatably positioned within cutting head 50 and is secured to the distal end of drive tube 18. Cutting head 50 has a cutting head opening 80 to anterior chamber 54.

Rotary cutting member 14 has a rotary cutting member opening 82 that generally matches the shape of cutting head opening 80. Those skilled in the art will recognize that the shapes of the two openings do not need to be the same. The exterior surface of rotary cutting member 14 is designed for an essentially intimate contact with the interior surface of cutting head 50, yet still providing for the ability to rotate when secured within cutting head 50. Together, cutting head opening 80 and rotary cutting member opening 82 create cutting tip opening 84, which, when even partially aligned, creates a conduit from the exterior of cutting head 80 to the interior of rotary cutting member 14, anterior chamber 54, and posterior passage 56 of the cutting head 50.

Cutting is achieved by rotation of rotary cutting member 14 within cutting head 50, creating the cutting tip opening 84, which varies in size as the blade spins about its axis. The maximum size of the cutting tip opening 84 and the length of time the cutter opening is at its maximum, is determined by the relative sizes of cutting head opening 80 and rotary cutting member opening 82 and the rotational speed of the rotary cutting member 14. Any nucleus tissue that has extended into cutting tip opening 84 is in the cutting path of rotary member 14, and is cut by the relative shearing action between the edges cutting head opening 80 and rotary cutting member opening 82. Tissue that is softer and relatively mobile, such as nucleus tissue, can extend into the cutting path of rotary cutting member 14. Should less mobile materials come in contact with the cutting tip, such as the annulus and endplate cartilage, they will not be able to extend into the cutting path of rotary cutting member 14.

Cutting head 50 is configured such that cutting head opening 80 does not extend beyond the central axis as shown in section A-A in FIG. 8, which results in a blunt distal tip and cutting of tissue from the side of cutting head 50 rather than at the distal tip. This blunt tip configuration resists penetration into fissures or other defects in the annulus tissue. Cutting head opening 80 positioned on the side of the cutting head provides a less aggressive cutting action with a harder tissue such as the annulus and cartilage as the force applied to the tissue by the sweeping motion as illustrated in FIGS. 6a through 6f is less than could be applied by directly engaging tissue with a cutting openings oriented normal to the apparatus axis 28.

As cutting occurs due to the relative motion of rotary cutting member 14 and cutting head 50, it should be recognized by those skilled in the art that cutting could be achieved by holding the rotary cutting member 14 stationary and rotating the cutting head 50 about axis 28. Additionally, it should be recognized that cutting can be achieved through relative rotation of rotary cutting member 14 and cutting head 50 in either direction about the central axis, or through alternating directions of rotation. Also, while straight edges are shown for the rotary cutting member 14 and cutting head 50 through the figures, it should be recognized that the cutting edges can be configured to have serrations, angles to provide additional ("razor") sharpness, or such features other than a straight edge.

While the relatively soft, mobile nucleus material may be able to passively extend into cutting tip opening 84 during general use and manipulation of the apparatus in the disc space, the nucleus tissue can be actively drawn into cutting tip opening 84 by the application of negative pressure (vacuum) through posterior passage 56 as illustrated in FIG. 8. The vacuum is provided to posterior passage 56 though drive tube lumen 48. The vacuum serves an additional purpose by evacuating cut tissue from cutting tip 11 and drive tube 18 to prevent clogging and allowing further cutting action. The continuous removal of cut nucleus tissue provided by the vacuum eliminates the need for repeated insertions into the disc space as required with the use of rongeurs and curettes.

Irrigation fluid (e.g., sterile saline) is directed into the cutting tip opening 84 by the irrigation port 64, which is connected to irrigation tube 62. Some form of saline is universally used to irrigate surgical wounds, and is critical to rehydrating the sticky dehydrated nucleus tissue to make it slippery prior to suction through posterior passage 56 and drive tube lumen 48 and preventing clogging of the apparatus. Excess saline that flows directly into cutting tip opening 11 also provides the advantage of keeping drive tube lumen 48 and the vacuum line wet, further preventing adhesion of the cut nucleus material.

The size of cutting tip opening 84, the rotational speed of rotary cutting member 14, the amount of vacuum applied to passage 56 though drive tube lumen 48 and the irrigation fluid flowrate through irrigation port 64 are all inter-related critical factors in successful cutting and continuous removal of nucleus tissue.

The relative sizes of the cutting head opening 80 and rotary cutting member opening 82, along with the rotary cutting member 14 rotational speed, determine the length of time that cutting tip opening 84 exists ("dwell time"). For any given cutting tip opening 84, a faster rotational speed will result in a shorter dwell time and a slower rotational speed will result in a longer dwell time. For any given rotational speed, a smaller cutting tip opening 84 will result in a shorter dwell time, and a larger cutting tip opening 84 will result in a longer dwell time. The dwell time is a critical factor in tissue cutting, as a longer dwell time may result in too much tissue extending into the cutting tip opening 84, and a shorter opening time may not allow tissue enough time to extend into cutting tip opening 84. The dwell time has been experimentally shown to be important. In the embodiment of the apparatus shown in FIGS. 7 and 8, with the selected set for a cutting head opening 80 and rotary cutting member opening 82 sizes, it was found that a rotational speed of 100 rpm resulted in cut tissue of a size ("cut size") greater than drive tube lumen 48, causing the device to clog. Using a rotational speed of over 1,000 rpm prevented any tissue from being cut, as the tissue was not mobile enough to extend into cutting tip opening 84 during the short time the opening existed during each rotation. Rotational speeds just under 1,000 rpm produced very small cut sizes that, while not resulting in a clogged device, took an excessive amount of time to remove the desired amount of tissue. In this particular example embodiment, a rotational speed of 200 rpm was found to provide an optimum balance between a cut size and speed of tissue removal. It should be understood that the rotational speed that provides the optimum balance for any another configuration may be different than 200 rpm.

For any given cutting tip opening 84 and blade rotational speed, the amount of vacuum applied to posterior passage 56 is critical to the function of the cutter. At the minimum of 0 atmospheres of vacuum (i.e., no vacuum applied) extension of even mobile tissue into the cutting path is passive and results only from manipulation of the cutter inside of the disc space. Tissue is cut more slowly, and once cut, is not extracted through drive tube lumen 48 and will clog the apparatus. With vacuum applied, the mobile nucleus tissue is actively drawn into cutting tip opening 84, and once cut, clogging is prevented by extracting the cut tissue through drive tube lumen 48 to expel it from the instrument. The critical nature of this feature has been shown experimentally, where the use of 0 atmospheres of vacuum in a prototype apparatus always resulted in clogging of the apparatus, but application of vacuum using a vacuum pump allowed the apparatus to be used without clogging. The theoretical maximum vacuum of 1 atmosphere cannot be achieved in practice due to the air flow through drive tube lumen 48, but vacuum levels measured at the pump experimentally were typically 0.5-0.8 atmospheres. It should be understood that vacuum levels outside of this range may still be effective with apparatus configurations other than that used in the experimental prototype.

For effective tissue cutting, regardless of the size of cutting tip opening 84, rotational speed, or vacuum level, hydration of the nucleus tissue near cutting tip opening 84 is critical to prevent clogging. It has been shown experimentally by use of a prototype apparatus without an irrigation port 64 located near cutting tip opening 84, with injection of saline into the disc nucleus of a human cadaver spine while the apparatus was otherwise functioning, at a distance of about 5 mm-10 mm from the cutting tip opening 84. It was found that the speed of fluid transport within the nucleus tissue was not sufficient to have a positive impact on the adhesive qualities of the tissue being cut, causing continual clogging of the apparatus. Attachment of an irrigation port 64 to the exterior of cutting head 50 as illustrated in FIG. 2, and connection of the attached irrigation tube 62 to a bag of saline under gravity feed as is normally found in the hospital, provided sufficient flow of saline to the tissue in and near the cutting path to cause the cut nucleus material to become extremely slippery and eliminating clogging of the apparatus. In an example embodiment of the apparatus with an irrigation port 64 having an inner diameter of 0.033 inches, it was found that having no saline flow always resulted in clogging, but a flowrate sufficient to provide a steady stream of saline from irrigation port 64 eliminated clogging. It should be understood that an apparatus with a configuration different from that of the prototype may require more or less saline flow to effectively prevent clogging. It was determined that saline that flowed directly into cutting tip opening 84 also provided the advantage of keeping drive tube lumen 48 wet, further preventing adhesion of the cut nucleus material. Movement of cut nucleus tissue was seen through the six feet of clear plastic tubing used to connect the apparatus to the vacuum trap positioned just prior to the vacuum pump.

In another embodiment, the cutting tip of an apparatus of the present invention has a 6 mm diameter round cutting tip with generally coincident oval-shaped openings in the side of cutting head 50 and rotary cutting member 14 that do not extend beyond the longitudinal axis of cutting head 50 and rotary cutting member 14, with cutting head opening 80 and rotary cutting member opening 82 dimensions of 5 mm along axis 28 and 3 mm normal to the axis 28 and with an operational rotational speed of the blade of 200 rpm, a >0.5 atmosphere vacuum applied to cutting tip opening 84 and a flowrate of saline through irrigation port 64 having a 0.033 inch diameter located near cutting tip opening 84 sufficient to provide a steady stream during operation.

The foregoing discussion discloses and describes merely exemplary embodiments of the present invention. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An apparatus for removing tissue from an intervertebral disc comprising:

an elongated guide tube defining a lumen extending through the elongated guide tube from a proximal opening at a proximal end of the elongated guide tube to a distal opening at a distal end of the elongated guide tube, the lumen including a bendable portion providing a bendable end near the distal end, the guide tube having a wall having a first bend control lumen therein and a second bend control lumen therein;

a first control wire within the first bend control lumen:

a second control wire within the second bend control lumen;

an actuator for moving at least one of the first control wire or the second control wire;

a cutting head housing slidably received within the distal opening at the distal end of the elongated guide tube, the cutting head housing positionable between a first retracted position and a second extended position relative to the distal end of the elongated guide tube;

a cutting member positioned within the cutting head housing, the cutting member adapted to rotate with respect to the cutting head;

a drive shaft rotatably received within the lumen and extending between the proximal opening in the guide tube and attached to the rotary cutting member;

a driver attached to the drive shaft near the proximal opening in the guide tube; the cutting head housing including a blunt end and having a cutting opening therein, the cutting opening including a cutting edge located between the blunt end and the distal end of the guide tube; and a control apparatus attached near the distal opening of the elongated guide, the control apparatus including a wire controller attached to the first control wire and the second control wire, the wire controller for varying the length of the first control wire and the second control wire to selectively bend the bendable end, the control apparatus further comprises an extension mechanism for selectively extending the cutting head housing with respect to the distal end of the guide tube.

2. The apparatus of claim 1, wherein the control apparatus includes a bend control lever.

3. The apparatus of claim 1 wherein the guide has a first extension lumen and a second extension lumen therein, the extension mechanism further comprising a first extension rod and a second extension rod attached between the cutting head housing and the control apparatus.

4. The apparatus of claim 3 wherein the control apparatus includes an extension control lever.

5. The apparatus of claim 3 wherein the control apparatus includes a control housing having a first actuator for controlling an amount of bending in the bendable member and having a second actuator for controlling the extension of the cutting head housing with respect to the guide.

6. The apparatus of claim 5 wherein the driver is located within the control housing.

7. The apparatus of claim 5 wherein the driver is remote from the control housing.

8. The apparatus of claim 5 wherein the control housing is pistol shaped and wherein the first actuator is a first trigger member, and the second actuator is a second trigger member.

9. The apparatus of claim 1 wherein the bendable end includes a plurality of subportions that are rotatably attached to one another.

10. The apparatus of claim 1 wherein the guide tube has a fluid passage therein, the fluid passage in fluid communication with a source of irrigation fluid.

11. The apparatus of claim 10 further including a vacuum source attached to the proximal end of the lumen, the vacuum source producing a vacuum at the distal end of the lumen and at the opening in the cutting head housing.

12. A method of removing tissue from an intervertebral space comprising:
   providing an apparatus for removing tissue from an intervertebral disc comprising an elongated guide tube defining a lumen extending through the elongated guide tube from a proximal opening at a proximal end of the elongated guide tube to a distal opening at a distal end of the elongated guide tube, the lumen including a bendable portion providing a bendable end near the distal end, the guide tube having a wall having a first bend control lumen therein and a second bend control lumen therein;
   a first control wire within the first bend control lumen;
   a second control wire within the second bend control lumen;
   an actuator for moving at least one of the first control wire or the second control wire;
   a cutting head housing slidably received within the distal opening at the distal end of the elongated guide tube, the cutting head housing positionable between a first retracted position and a second extended position relative to the distal end of the elongated guide tube;
   a cutting member positioned within the cutting head housing, the cutting member adapted to rotate with respect to the cutting head;
   a drive shaft rotatably received within the lumen and extending between the proximal opening in the guide tube and attached to the rotary cutting member;
   a driver attached to the drive shaft near the proximal opening in the guide tube; the cutting head housing including a blunt end and having a cutting opening therein, the cutting opening including a cutting edge located between the blunt end and the distal end of the guide tube; and
   a control apparatus attached near the distal opening of the elongated guide, the control apparatus including a wire controller attached to the first control wire and the second control wire, the wire controller for varying the length of the first control wire and the second control wire to selectively bend the bendable end, the control apparatus further comprises an extension mechanism for selectively extending the cutting head housing with respect to the distal end of the guide tube;
   positioning the bendable end of the elongated guide tube within an intervertebral disc space with the blunt end and a portion of the cutting head housing near an annulus of a disc;
   rotating the cutting member within the cutting head housing while bending the bendable end;
   controllably bending the bendable end away from the annulus of the disc, thereby imparting a sweeping motion within the intervertebral space with the cutting head housing in a first retracted position relative to the bendable end of the elongated guide tube to cut a nucleus pulposus of the interverbral disc;
   extending the cutting head housing from the first retracted position to the second extended position relative to the bendable end of the elongated guide tube: and
   controllably bending the bendable end away from the annulus of the disc, thereby imparting a sweeping motion within the intervertebral space with the cutting head housing in a second extended position relative to the bendable end of the elongated guide tube to cut the nucleus pulposus of the interverbral disc.

13. The method of claim 12 further comprising;
   pumping an irrigation fluid through the walls of the elongated guide tube; and
   producing a vacuum at the end of the guide to remove material and irrigation fluid through the elongated guide tube.

14. An apparatus for removing tissue from an intervertebral disc comprising:
   an elongated guide tube defining a lumen extending through the elongated guide tube from a proximal opening at a proximal end of the elongated guide tube to a distal opening at a distal end of the elongated guide tube, the lumen including a bendable portion providing a bendable end near the distal end, the guide tube having a wall having a first bend control lumen therein and a second bend control lumen therein;
   a first control wire within the first bend control lumen;
   a second control wire within the second bend control lumen;
   an actuator for moving at least one of the first control wire or the second control wire;
   a cutting head housing slidably received within the distal opening at the distal end of the elongated guide tube, the cutting head housing positionable between a first retracted position and a second extended position relative to the distal end of the elongated guide tube;
   a cutting member positioned within the cutting head housing, the cutting member adapted to rotate with respect to the cutting head;
   a drive shaft rotatably received within the lumen and extending between the proximal opening in the guide tube and attached to the rotary cutting member; and
   a driver attached to the drive shaft near the proximal opening in the guide tube; the cutting head housing including a blunt end and having a cutting opening therein, the cutting opening including a cutting edge located between the blunt end and the distal end of the guide tube;
   a control apparatus attached near the distal opening of the elongated guide, the control apparatus including a wire controller attached to the first control wire and the second control wire, the wire controller for varying the length of the first control wire and the second control wire to selectively bend the bendable end, the control apparatus further comprises an extension mechanism for selectively extending the cutting head housing with respect to the distal end of the guide tube;
   the cutting member and cutting head housing each defining an opening on a side of the cutting member and a side of the cutting head that does not extend beyond a central axis of the cutting member and the cutting head housing, such that each opening is aligned during a portion of a rotation of the cutting member about the central axis to provide a passage between the outside of the cutting head housing and the inside of the cutting member;
   a fluid passage directed into the inside of the cutting member, the fluid passage in fluid communication with a source of irrigation fluid; and
   a vacuum source attached to the proximal end of the lumen of the elongated guide tube, the vacuum source producing a vacuum at the distal end of the lumen and at the opening in the cutting head housing.

15. The apparatus of claim 14 wherein the size of the openings in the cutting member and cutting head, the rotational speed of the cutting member, the flow rate of the irrigation fluid through the fluid passage, and the amount of vacuum applied to the lumen of the elongated tube are adapted to allow nucleus pulposus tissue to be cut and removed preferentially over surrounding annulus fibrosus and cartilage tissue.

16. A method of removal of tissue from an intervertebral disc comprising:

providing an apparatus for removing tissue from an intervertebral disc comprising an elongated guide tube defining a lumen extending through the elongated guide tube from a proximal opening at a proximal end of the elongated guide tube to a distal opening at a distal end of the elongated guide tube, the lumen including a bendable portion providing a bendable end near the distal end, the guide tube having a wall having a first bend control lumen therein and a second bend control lumen therein;

a first control wire within the first bend control lumen; a second control wire within the second bend control lumen; an actuator for moving at least one of the first control wire or the second control wire; a cutting head housing slidably received within the distal opening at the distal end of the elongated guide tube, the cutting head housing positionable between a first retracted position and a second extended position relative to the distal end of the elongated guide tube;

a cutting member positioned within the cutting head housing, the cutting member adapted to rotate with respect to the cutting head;

a drive shaft rotatably received within the lumen and extending between the proximal opening in the guide tube and attached to the rotary cutting member;

a driver attached to the drive shaft near the proximal opening in the guide tube;

the cutting head housing including a blunt end and having a cutting opening therein, the cutting opening including a cutting edge located between the blunt end and the distal end of the guide tube; and a control apparatus attached near the distal opening of the elongated guide, the control apparatus including a wire controller attached to the first control wire and the second control wire, the wire controller for varying the length of the first control wire and the second control wire to selectively bend the bendable end, the control apparatus further comprises an extension mechanism for selectively extending the cutting head housing with respect to the distal end of the guide tube;

positioning the cutting head housing within the intervertebral disc space; rotating the cutting member to cut nucleus pulposus tissue from within the disc space;

pumping irrigation fluid through a fluid passage directed into the inside of the cutting member;

producing a vacuum at the end of the proximal end of the lumen of the elongated tube to remove the cut material and irrigation fluid through the lumen of the elongated tube; and selecting the cutting member rotational speed, irrigation fluid flow rate, and amount of vacuum such that these parameter levels, in combination with the size of the openings in the cutting member and cutting head, to preferentially cut and remove nucleus pulposus tissue over surrounding annulus fibrosus and cartilage tissue.

* * * * *